US011369671B2

(12) United States Patent
Szathmary et al.

(10) Patent No.: US 11,369,671 B2
(45) Date of Patent: Jun. 28, 2022

(54) VACCINE TO PREVENT MYCOPLASMAL INFECTIONS IN WATERFOWL

(71) Applicant: GalenBio, Inc., Carlsbad, CA (US)

(72) Inventors: Susan Szathmary, Carlsbad, CA (US); Laszlo Stipkovits, Carlsbad, CA (US)

(73) Assignee: GalenBio, Inc., Carlsbad, CA (US)

( * ) Notice: Subject to any disclaimer, the term of this patent is extended or adjusted under 35 U.S.C. 154(b) by 0 days.

(21) Appl. No.: 14/427,259

(22) PCT Filed: Sep. 9, 2013

(86) PCT No.: PCT/US2013/058779
§ 371 (c)(1),
(2) Date: Mar. 10, 2015

(87) PCT Pub. No.: WO2014/039978
PCT Pub. Date: Mar. 13, 2014

(65) Prior Publication Data
US 2016/0082094 A1    Mar. 24, 2016

Related U.S. Application Data

(60) Provisional application No. 61/699,095, filed on Sep. 10, 2012.

(51) Int. Cl.
*A61K 39/02* (2006.01)
*A61K 39/12* (2006.01)
*A61K 39/00* (2006.01)

(52) U.S. Cl.
CPC .......... *A61K 39/02* (2013.01); *A61K 39/0241* (2013.01); *A61K 39/12* (2013.01); *A61K 2039/521* (2013.01); *A61K 2039/54* (2013.01); *A61K 2039/545* (2013.01); *A61K 2039/55* (2013.01); *A61K 2039/552* (2013.01); *A61K 2039/55505* (2013.01); *A61K 2039/55566* (2013.01); *A61K 2039/55572* (2013.01); *A61K 2039/55594* (2013.01); *A61K 2039/70* (2013.01); *C12N 2750/14334* (2013.01)

(58) Field of Classification Search
None
See application file for complete search history.

(56) References Cited

U.S. PATENT DOCUMENTS

| 3,917,819 A * | 11/1975 | Yoshioka ........... A61K 39/0241 424/264.1 |
| 5,004,607 A | 4/1991 | Ragland et al. |
| 5,338,543 A | 8/1994 | Fitzgerald et al. |
| 5,565,205 A | 10/1996 | Petersen et al. |
| 6,001,348 A | 12/1999 | Witvliet |
| 6,113,916 A | 9/2000 | Bhogal et al. |
| 6,548,069 B2 | 4/2003 | Hymas et al. |
| 6,814,971 B2 | 11/2004 | Roberts et al. |
| 7,371,395 B2 | 5/2008 | Parisot et al. |
| 7,416,734 B2 | 8/2008 | Leonard et al. |
| 7,608,279 B2 | 10/2009 | Parisot et al. |
| 7,691,368 B2 | 4/2010 | Parisot et al. |
| 2006/0093627 A1 | 5/2006 | Lee |
| 2008/0014221 A1 | 1/2008 | Royer et al. |
| 2010/0062019 A1 | 3/2010 | Parisot et al. |
| 2012/0021005 A1 | 1/2012 | Kleven et al. |

FOREIGN PATENT DOCUMENTS

| WO | 2005009462 A2 | 2/2005 |
| WO | 2006/081576 | 8/2006 |
| WO | 2007103042 A2 | 9/2007 |
| WO | 2010085611 A2 | 7/2010 |
| WO | 2010/119112 | 10/2010 |

OTHER PUBLICATIONS

Dupius et al. (Ann. N.Y. Acad. Sci., 1081:202-205, 2006).*
M. Chen et al. "Vaccination with Recombinant Alphavirus or Immune-Stimulating Complex Antigen Against Respiratory Syncytial Virus" The Journal of Immunology, 2002, 10 pages.
M. Dobos-Kovács et al. "Salpingitis in geese associated with *Mycoplasma* sp. strain 1220" Avian Pathol, 2010, 19 pages.
European Office Action for related European Patent Application No. 13834504.6-1412 dated May 24, 2016, 8 Pages.
Dobos-Kovacs et al., "Salpingitis in geese associated with *Mycoplasma* sp. strain 1220", Avian Pathology, Jun. 1, 2009, vol. 38, No. 3, pp. 239-243.
Nascimento et al., "Avian Mycoplasmosis Update," Brazil. J. Poultry Sci. 7: 1-9 (2005), retrieved on Oct. 19, 2017, from "http://www.scielo.br/scielo.php?pid=S1516-635X2005000100001&script=sci_arttext&tlng=pt", 9 pages.
Wilson et al., "Evaluation of Mycoplasma Inactivation during Production of Biologies: Egg-Based Viral Vaccines as a Model," Applied and Environmental Microbiology, vol. 76, No. 9, May 2010, pp. 2718-2728.
Kleven, "News—Summary of Discussions, Avian Mycoplasma Team, International Research Program on Comparative Mycoplasmology, International Organization of Mycoplasmology, University of Ljubljana, Domžale, Slovenia, Sep. 29-Oct. 1, 1993", Avian Pathology (1994) 23, pp. 587-594.

\* cited by examiner

*Primary Examiner* — Brian Gangle
(74) *Attorney, Agent, or Firm* — Ditthavong, Steiner, Mlotkowski

(57) ABSTRACT

An improved vaccine for immunization of waterfowl such as ducks and geese comprises an inactivated strain of a *mycoplasma* infecting waterfowl, such as *Mycoplasma* sp. strain 1220; the vaccine can include an excipient and an adjuvant. Methods for immunization of waterfowl with the vaccine are also described.

7 Claims, No Drawings

US 11,369,671 B2

VACCINE TO PREVENT MYCOPLASMAL INFECTIONS IN WATERFOWL

CROSS-REFERENCES

This application claims the benefit of U.S. Provisional Application Ser. No. 61/699,095 by S. Szathmary et al., entitled "Vaccine to Prevent *Mycoplasma* Infection in Waterfowl," and filed on Sep. 10, 2012, the contents of which are incorporated herein in their entirety by this reference.

FIELD OF THE INVENTION

The present invention relates to the fields of microbiology and immunology. In particular, this invention relates to novel vaccines for protection against mycoplasmal disease in waterfowl, compositions for the diagnosis of such infections, and methods of diagnosis of mycoplasmal disease in waterfowl and vaccination of waterfowl against mycoplasmal disease.

BACKGROUND OF THE INVENTION

*Mycoplasmas* are small prokaryotic organisms (0.2 to 0.3 μM) belonging to the class Mollicutes, whose members lack a cell wall and have a small genome size that is intermediate in size between the typical genome size of a bacterium and they typical genome size of a virus. These *mycoplasmas* are the smallest of the free-living microorganisms and are enveloped with only a cell membrane, which allows for varying morphological shapes and unique growth requirements; they lack the conventional cell wall of bacteria.

The Mollicutes include more than 100 species of *mycoplasma*. *Mycoplasma* species are the causative agents of several diseases in human and non-human animals as well as in plants. The *mycoplasmas*, including the 1220 type of *mycoplasma*, *Mycoplasma anseris*, *Mycoplasma anatis*, *Mycoplasma synoviae*, and other mycoplasmal species, are opportunistic microorganisms, and are responsible for significant disease conditions in geese and ducks. *Mycoplasmas* are associated with respiratory disease, developing airsacculitis, peritonitis, or joint lesions. They can also cause mortality of birds and embryos, decrease of body weight, phallus inflammation, decrease of egg production, and increase of egg infertility. Mycoplasmal infection occurs in all countries where large goose and duck flocks exist. Even though several species of *mycoplasmas* have been isolated in waterfowl, some of the prevalent strains are the 1220 type of *mycoplasma*, *Mycoplasma anseris*, *Mycoplasma anatis*, and *Mycoplasma cloacale*.

Diseases caused by *mycoplasmas* are often resistant to antimicrobial therapy, leaving no effective means of treatment. In addition very few drugs are registered for use in duck and geese. Consequently, this has enormous economic implications in the waterfowl industry where losses are measured by the value of the dead birds, decrease of egg production and body weight, increased embryo mortality and egg infertility, as well as the existence of culled ganders due to phallus inflammation. Mycoplasmal infections in waterfowl are increasing in prevalence worldwide.

The raising of waterfowl, especially ducks and geese, is of enormous economic importance in many countries. Duck and goose are esteemed foods in many cuisines and the meat from ducks or geese is considered a delicacy of high value. Therefore, controlling pathogens in waterfowl is of extreme importance.

An effective strategy for preventing and managing diseases caused by mycoplasmal infection in goose and duck farms is by vaccination with killed vaccine since very few drugs are registered for usage for geese and ducks. The advantage of killed vaccines, in general, is that no living *mycoplasmas* are present, which can, in association with other viruses and bacteria frequently present in these birds cause disease.

Therefore, there is a need for an effective vaccine against mycoplasmal infection in waterfowl, particularly in ducks and geese. In particular, there is a need for an effective vaccine against mycoplasmal infections. Preferably, such an effective vaccine would be a killed or inactivated vaccine.

SUMMARY OF THE INVENTION

The present invention is based, in part, on successful isolation and characterization of *mycoplasmas* present in geese and ducks and selection of suitable, immunologically active strains of waterfowl *mycoplasma*, such as the 1220 type of *mycoplasma*, *Mycoplasma anatis*, *Mycoplasma anseris*, *Mycoplasma gallisepticum*, *Mycoplasma synoviae*, *Mycoplasma cloacale*, *Mycoplasma imitans*, and *Acholeplasma modicum*.

Accordingly, the present invention is directed to select strains having ability to split glucose or arginine, or reduce tetrazolium, or produce film and spotting on the surface of solid media, or hemolyze goose erythrocytes.

The present invention also provides vaccine compositions comprising prepared antigen from any strains of the invention and adjuvant, as well as methods of vaccinating the animal against infection and measuring immunity or the serological response induced by vaccines.

One aspect of the present invention is a vaccine that is protective against mycoplasmal disease of a waterfowl comprising at least one inactivated waterfowl mycoplasmal strain. Typically, the vaccine further comprises at least one pharmaceutically acceptable excipient. The vaccine can also further comprise at least one pharmaceutically acceptable adjuvant. Typically, the vaccine is protective against mycoplasmal infection for a waterfowl species selected from a duck and a goose.

The inactivated waterfowl *mycoplasma* strain can be *Mycoplasma* sp. strain 1220, *Mycoplasma anseris*, *Mycoplasma anatis*, *Mycoplasma cloacale*, *Mycoplasma imitans*, *Mycoplasma gallisepticum*, *Mycoplasma synoviae*, *Acholeplasma modicum*, or *Acholeplasma axantum*. A particularly preferred inactivated waterfowl *mycoplasma* strain is *Mycoplasma* sp. strain 1220.

The vaccine can comprise two or more strains of inactivated waterfowl *mycoplasma*, or three or more strains of inactivated waterfowl *mycoplasma*.

The adjuvant, if used, can be selected from the group consisting of: an oil; an aluminum hydroxide-oil emulsion; a mineral oil-water emulsion; a vegetable oil-water emulsion; a fish oil-water emulsion, a water-oil-emulsion; incomplete Freund's adjuvant; *Escherichia coli* J5, dextran sulfate; iron oxide; sodium alginate; a synthetic polymer; CARBOPOL® (polyacrylic acid); a polyamino acid; a copolymer of two or more amino acids; saponin; carrageenan; an emulsion of mycobacterial cell wall fractions comprising trehalose dimycolate and muramyl dipeptide; N,N-dioctadecyl-N',N'-bis(2-hydroxyethyl)propanediamine; a long-chain polydisperse β(1,4)-linked mannan polymer interspersed with O-acetylated groups; a deproteinized cell wall extract from a non-pathogenic strain of *Mycobacterium*;

mannide monooleate; paraffin oil; muramyl dipeptide β-propiolactone; aluminum hydroxide; and aluminum phosphate.

The mycoplasmal strain or strains can be inactivated by an inactivating agent or method selected from the group consisting of: formalin, azide, freeze-thaw, sonication, heat treatment, sudden pressure drop, detergent, lysozyme, phenol, proteolytic enzymes, β-propiolactone, thimerosal, and binary ethyleneimine.

The vaccine can further comprise an inactivated non-mycoplasmal microorganism or an antigen from a non-mycoplasmal microorganism. The non-mycoplasmal organism can be selected from the group consisting of *Staphylococcus aureus, Pasteurella haemolytica, Pasteurella multocida, Escherichia coli, Salmonella, Rimerella antipestifer, Chlamydophila, Erysipelothrix rhusiopathiae, Listeria monocytogenes*, goose parvovirus, reticuloendotheliosis virus, duck enteritis virus, and circovirus.

Typically, the vaccine is protective of disease in a species of goose or duck following systemic or mucosal administration. In one alternative, the vaccine provides immunity after a single administration in the waterfowl against *mycoplasmas* capable of causing disease in the waterfowl. In another alternative, the vaccine provides immunity after repeated administration in the waterfowl against *mycoplasmas* capable of causing disease in the waterfowl.

Typically, the vaccine provides immunity after repeated administration in the waterfowl against *mycoplasmas* capable of causing disease in the waterfowl. Typically, the serological response is detectable by an ELISA test, and the ELISA test can be used for detecting natural mycoplasmal infection and for controlling immunization of waterfowl.

In one alternative, the mycoplasmal strain is isolated from a specific farm to provide a farm-specific vaccine.

In one alternative, the vaccine is for use in a flock of waterfowl being treated with medication prior to or during vaccination; the medication can be at least one antibiotic.

Particular examples of the vaccine include: (1) a vaccine comprising inactivated *Mycoplasma* sp. strain 1220, *Mycoplasma anatis*, and *Mycoplasma anseris*, each at $10^6$ cfu with incomplete Freund's adjuvant in a total volume of 0.1 to 1 mL per unit dose; (2) a vaccine comprising inactivated *Mycoplasma anseris* at $10^6$ cfu with incomplete Freund's adjuvant in a total volume of 0.1 to 1 mL per unit dose; (3) a vaccine comprising inactivated *Mycoplasma* sp. strain 1220 at $10^6$ cfu with incomplete Freund's adjuvant in a total volume of 0.1 to 1 mL per unit dose; (4) a vaccine comprising inactivated *Mycoplasma anatis, Mycoplasma anseris*, and *Mycoplasma imitans* each at $10^5$ cfu with incomplete Freund's adjuvant in a total volume of 0.1 to 1 mL per unit dose; (5) a vaccine comprising inactivated *Mycoplasma anatis* at $10^5$ cfu with incomplete Freund's adjuvant in a total volume of 0.1 to 1 mL per unit dose; (6) a vaccine comprising inactivated *Mycoplasma* sp. strain 1220 and *Mycoplasma imitans* each at $10^6$ cfu with incomplete Freund's adjuvant in a total volume of 0.1 to 1 mL per unit dose; (7) a vaccine comprising inactivated *Mycoplasma cloacale* and *Mycoplasma anatis* each at $10^6$ cfu and killed *Escherichia coli* bacteria at $10^5$ cfu with incomplete Freund's adjuvant in a total volume of 0.1 to 1 mL per unit dose; (8) a vaccine comprising comprises inactivated *Mycoplasma anatis* and *Acholeplasma axantum* each at $10^6$ cfu with incomplete Freund's adjuvant in a total volume of 0.1 to 1 mL per unit dose; and (9) a vaccine comprising inactivated *Mycoplasma* sp. strain 1220 and *Mycoplasma cloacale* each at $10^6$ cfu with incomplete Freund's adjuvant in a total volume of 0.1 to 1 mL per unit dose.

The vaccine can further comprise a microparticulate carrier. The microparticulate carrier can be a polysaccharide; preferably, the polysaccharide is agarose. Typically, the microparticulate carrier comprises particles less than about 10 μm in diameter; preferably, the microparticulate carrier comprises particles less than about 5 μm in diameter. When the vaccine comprises a microparticulate carrier, the vaccine can also further comprise at least one pathogen associated molecular pattern (PAMP) selected from the group consisting of a TLR 1 receptor agonist, a TLR 2 receptor agonist, a TLR 3 receptor agonist, a TLR 4 receptor agonist, a TLR 5 receptor agonist, a TLR 6 receptor agonist, a TLR 7 receptor agonist, a TLR 8 receptor agonist, a TLR 9 receptor agonist, a NOD-1 agonist, a NOD-2 agonist, an agonist for DC-SIGN, an agonist for L-SIGN, and an agonist for a mannose receptor. The mycoplasmal antigen or antigens, and, if present, the PAMP, can be covalently or noncovalently associated with the microparticulate carrier.

Another aspect of the present invention is a method of immunizing a waterfowl against infectious disease comprising administering to a bird an immunogenic amount of at least one mycoplasmal strain to elicit a protective immune response in the bird. Typically, the method comprises administering a vaccine comprising at least one inactivated strain to elicit a protective immune response in the bird; the vaccine is a vaccine according to the present invention as described above.

Typically, the result of vaccination is such that the incidence of disease caused by waterfowl *mycoplasma* in a flock to which the vaccine is administered is greater before vaccination than after vaccination. Typically, vaccination of breeding waterfowl prevents at least one deleterious effect caused by mycoplasmal infection selected from the group consisting of: (1) reduction of body weight; (2) development of pathological lesions of respiratory and reproductive organs; and (3) colonization of organs of birds induced by *mycoplasma* infection. The deleterious effect caused by mycoplasmal infection and prevented by vaccination can be the development of pathological lesions of respiratory and reproductive organs and the pathological lesions of reproductive organs are salpingitis and inflammation of the phallus. Typically, vaccination of breeding waterfowl reduces mycoplasmal infection of birds and embryos and normalizes egg production that would otherwise be reduced by mycoplasmal infection. Typically, vaccination of breeding waterfowl increases maternal immunity of goslings originating from immunized breeders. Typically, vaccination of breeding waterfowl reduces egg infertility caused by mycoplasmal infection. Typically, vaccination of breeding waterfowl increases weight gains and reduces mortality of goslings originating from immunized breeders.

In one alternative, the vaccine is administered to young animals and increases their immunity against mycoplasmal infection.

In one alternative, the method can comprise comprising the step of co-administering at least one additional *mycoplasma*; the at least one additional *mycoplasma* can be selected from the group consisting of *Mycoplasma* sp. strain 1220, *Mycoplasma anseris, Mycoplasma anatis, Mycoplasma cloacale, Mycoplasma imitans, Mycoplasma gallisepticum, Mycoplasma synoviae, Acholeplasma modicum*, and *Acholeplasma axantum*.

In another alternative, the method can comprise the step of co-administering at least one additional bacterin or bacterial antigen. The bacterin or bacterial antigen can be selected from the group consisting of *Staphylococcus aureus, Pasteurella haemolytica, Pasteurella multocida*,

*Escherichia coli, Salmonella, Rimerella antipestifer, Chlamydophila, Erysipelothrix rhusiopathiae, Listeria monocytogenes*, and *Chlamydophila psittaci.*

In yet another alternative, the method can comprise the step of co-administering at least one live or inactivated virus or viral antigen; the live or inactivated virus or viral antigen can be selected from the group consisting of goose parvovirus, influenza virus, poliovirus, enteritis virus, circovirus, West Nile virus, hepatitis virus, and reticuloendotheliosis virus. A particularly significant virus for co-administration is goose parvovirus.

Typically, the vaccine is administered subcutaneously; however other routes of administration, such as mucosal administration, can be employed.

In one alternative, following initial administration of the vaccine, at least one additional dose of the vaccine is administered as a booster.

Yet another aspect of the invention is an ELISA assay method for detection of an antigen characteristic of a mycoplasmal species, strain, or biotype, comprising the steps of:

(1) coating a solid support with a first, unlabeled, antibody specific for the antigen;

(2) contacting the coated solid support with a sample that may contain the antigen to bind the antigen to the first unlabeled antibody bound to the solid support;

(3) contacting the antigen bound to the antibody bound to the solid support with a second, labeled, antibody specific for the antigen; and (4) quantitating the second, labeled, antibody bound to the solid support in order to quantitate the antigen in the sample.

The ELISA method can be used to quantitate an antigen, to determine efficacy of immunization, or for controlling immunization of waterfowl.

DETAILED DESCRIPTION OF THE INVENTION

The present invention is directed to strains of *mycoplasmas* in waterfowls such as the type 1220 *mycoplasmas, Mycoplasma anatis, Mycoplasma anseris, Mycoplasma cloacale, Mycoplasma synoviae, Mycoplasma imitans*, and other mycoplasmal species and strains that infect waterfowl and that are suitable for use in vaccine formulations. The strains of *mycoplasmas* of the present invention exhibit strong antigenicity, which can be detected by quantitative antibody-based methods such as Western blotting, and enzyme-linked immunosorbent assays (ELISAs), in which an antibody is used which detects and binds to the protein of interest.

The type 1220 *mycoplasmas* are particularly prevalent in geese, and are described in M. Dobos-Kovács et al., "Salpingitis in Geese Associated with *Mycoplasma* sp. Strain 1220," *Avian Pathol.* 38: 239-243 (2009), incorporated herein by this reference. Other *mycoplasmas*, such as *M. anseris, M. anatis, M. cloacale*, and *M. synoviae* are also particularly prevalent in geese.

A number of mycoplasmal species have the property of producing films and spots on the surface of solid media. This is due to an enzymatic reaction between the *mycoplasma* and lipids in serum present in the medium. As a result of this reaction, cholesterol and phospholipids are produced which precipitate in a reaction with $Ca^{2+}$ ions to form spots and films. This phenomenon has been used for an aid in classifying and identifying mycoplasmal species.

In accordance with the purposes of this invention, as embodied and broadly described herein, this invention, in one aspect, provides a vaccine composition which is protective against the *mycoplasma* disease in waterfowl, such as duck and goose species, comprising one or more of inactivated waterfowl *mycoplasmas*, including but not limited to the 1220 strain of *mycoplasma*, or *M. anseris*, or *M. imitans* and a pharmaceutically acceptable excipient. The term "inactivated," also referred to as "killed," means that the microorganisms are treated by any of several means known to the art so that they no longer grow or reproduce, but that the microorganisms are still capable of eliciting an immune response in the target animal. Examples of inactivating agents or methods include, but are not limited to: formalin, azide, freeze-thaw, sonication, heat treatment, sudden pressure drop, detergents (especially non-ionic detergents), lysozyme, phenol, proteolytic enzymes, β-propiolactone, thimerosal (described in U.S. Pat. No. 5,338,543 to Fitzgerald et al., incorporated herein by this reference), and binary ethyleneimine (described in U.S. Pat. No. 5,565,205 to Petersen et al., incorporated herein by this reference). In a specific embodiment, the *mycoplasma* strains used in the vaccine are inactivated with β-propiolactone (BPL) or by formalin.

BPL has the structure shown below in Formula (I):

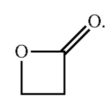

(I)

Other inactivation methods are known in the art and are within the scope of the present invention. These include glutaraldehyde, as described in U.S. Pat. No. 6,548,069 to Hymas et al., incorporated herein by this reference.

The term "pharmaceutically acceptable" means a material that is not biologically or otherwise undesirable, i.e., the material may be administered to an animal along with the immunogenic material (i.e. inactivated 1220 type of *mycoplasma* biotypes) without causing any undesirable biological effects or interacting in a deleterious manner with any of the other components of the vaccine in which it is contained. Examples of such pharmaceutically acceptable excipients include water and physiological saline (for further examples, see Arnon, R. (Ed.) Synthetic Vaccines 1:83-92, CRC Press, Inc., Boca Raton, Fla., 1987, incorporated herein by this reference).

Additional excipients are known in the art. For example, U.S. Pat. No. 5,004,607 to Ragland et al., incorporated herein by this reference, discloses the use of 0.1% to 0.3% of iota carrageenan in phosphate buffer as an excipient. U.S. Pat. No. 7,371,395 to Parisot et al., incorporated herein by this reference, discloses the use of glucose, polyols, carbohydrates, amino acids, peptides, antioxidants, bactericides, and bacteriostatic compounds. U.S. Pat. No. 7,691,368 to Parisot et al., incorporated herein by this reference, discloses the use of wetting agents and viscosity enhancing agents.

Other ingredients compatible with the inactivated mycoplasmal strain and with any adjuvant included can also be used. For example, preservatives, dyes, and chelators can be added, such as described in U.S. Pat. No. 5,565,205, by Petersen et al., incorporated herein by this reference. A suitable chelator is EDTA. U.S. Pat. No. 6,113,916 to Bhogal et al., incorporated by this reference, discloses the use of pH adjusting and buffering agents and emulsifiers.

The invention disclosed herein is based in part on the discovery that the waterfowl *mycoplasma* infection in the field comprises individual mixtures of *mycoplasma* species or biotypes. The term biotype means a variant of a species, i.e. a strain, that can be distinguished by one or more characteristics, such as, but not limited to, DNA polymorphisms or serological typing. As applied to *mycoplasmas*, the term "biotype" is defined in U.S. Pat. No. 6,548,069 to Hymas et al., incorporated herein by this reference, as a group of strains or isolates of the same species with common genetic characteristics; that is, members of a particular biotype are genetically identical. One means of classifying members of a species according to biotype is based upon DNA relatedness. DNA relatedness may be determined by a number of conventional methods including, but not limited to, PCR analysis, electrophoresis patterns, fingerprinting methods, and Random Amplified Polymorphic DNA (RAPD) analysis. The use of RAPD analysis is described in G. A. Penner et al., "Reproducibility of Random Amplified Polymorphic DNA (RAPD) Analysis Among Laboratories," *Genome Res.* 2: 341-345 (1993), incorporated herein by this reference. Biotypes can also be classified and distinguished by other techniques, such as ribosomal RNA sequence variation, serological typing, or toxin production, as disclosed in U.S. Pat. No. 7,416,734 to Leonard et al., incorporated herein by this reference. Additionally, endonuclease digestion of DNA prepared from different strains of the same mycoplasmal species results in different DNA digestion profiles that can be used for differentiation of the various strains.

Serological typing for *mycoplasma* can be carried out by conventional methods, such as the slide plate agglutination method or enzyme-linked immunosorbent assays (ELISA), as described in S. Levisohn & S. H. Kleven, "Avian Mycoplasmosis (*Mycoplasma gallisepticum*)," *Rev. Sci. Tech.* 19: 425-442 (2000), incorporated herein by this reference.

Procedures for ELISA assays are well known in the art. In general, antibodies to mycoplasmal antigens, either polyclonal antibodies or monoclonal antibodies, can be prepared by standard techniques, such as those disclosed in E. Harlow & D. Lane, "Antibodies: A Laboratory Manual" (Cold Spring Harbor Laboratory, 1988), incorporated herein by this reference. Polyclonal antibodies can be produced by immunization of suitable antibody-producing animals such as rabbits, rats, mice, hamsters, guinea pigs, sheep, or goats with the polypeptides. Typically, immunization is performed with the use of an adjuvant such as Freund's adjuvant, aluminum hydroxide adjuvant, Lipid A, muramyl dipeptide, SAF, or RAS. Once polyclonal antibodies have been prepared and antibody-secreting lymphocytes are available, these cells can be fused with appropriate myeloma fusion partners and hybridomas can be selected that grow in culture and produce monoclonal antibodies of the appropriate specificity according to the protocol originally described by Köhler and Milstein. The steps required for fusion, selection, and screening are well known in the art and are described, for example, in E. Harlow & D. Lane, "Antibodies: A Laboratory Manual" (Cold Spring Harbor Laboratory, 1988), incorporated herein by this reference.

The ELISA assay as described herein is a form of sandwich immunoassay. In the ELISA assay, a non-labeled antibody is attached to the surface of a solid phase, such as that of a microtiter well, a magnetic particle, or a plastic bead. This attachment facilitates the separation of bound labeled reactants from free labeled reactants; since only the bound labeled reactants (labeled antibody) bound to the antigen in the sandwich need to be detected or determined.

A number of suitable enzymes are known in the art for use in ELISA assays. These enzymes include, but are not limited to, alkaline phosphatase, horseradish peroxidase, glucose 6-phosphate dehydrogenase, and β-galactosidase. Other enzyme labels are also known in the art. Such labels include, but are not necessarily limited to, acetate kinase, β-lactamase, glucose oxidase, firefly luciferase, laccase, Renilla luciferase, and xanthine oxidase. Enzyme-labeled antibodies can be prepared by covalent coupling procedures involving reagents such as, but not limited to, glutaraldehyde, N-succinimidyl 3-[pyridyl] propionate, carbodiimides, carbonyldiimidazole, and other cross-linking reagents known in the art, such as those described in G. T. Hermanson, "Bioconjugate Techniques" (Academic Press, San Diego, 1996), pp. 630-637, incorporated herein by this reference. As another alternative, recombinant antibody conjugates can be prepared by genetic engineering techniques known in the art, the conjugates being produced by transcription and translation of gene fusions.

In many cases, the enzyme in the enzyme-labeled antibody in ELISA produces a product that is detected and/or quantitated photometrically, such as by spectroscopy. However, in some alternatives, the enzyme produces a product that is monitored and/or quantitated by other means, such as detection and/or quantitation of fluorescence, bioluminescence, or chemiluminescence. For example, immunoassays that use horseradish peroxidase as the enzyme label can be assayed by the detection of chemiluminescence using a mixture of luminol, peroxide, and an enhancer such as p-iodophenol or by using an acridan derivative. Umbelliferone phosphate is a nonfluorescent substrate that is converted to the highly fluorescent umbelliferone by the catalytic activity of the enzyme alkaline phosphatase. Another sensitive assay using an alkaline phosphatase label uses a chemiluminescent adamantyl 1,2-dioxetane aryl phosphate substrate, which is dephosphorylated by the catalytic activity of alkaline phosphate and decomposes with a concomitant long-lived glow of light, such that the detection limit for alkaline phosphatase using this assay can be as low as 1 zeptomole ($10^{-21}$ moles). In another alternative, an enzyme cascade is used. The advantage of the use of an enzyme cascade is that it combines the amplification properties of two enzymes—the alkaline phosphatase present in the antibody label and the second enzyme, alcohol dehydrogenase, in the assay reagent, thereby producing an extremely sensitive assay. For example, the alkaline phosphatase can dephosphorylate NADP to NAD, which then takes part in a reaction catalyzed by alcohol dehydrogenase and the enzyme diaphorase in which ethanol is oxidized to acetaldehyde and p-iodonitrotetrazolium violet is reduced to the detectable formazan by the catalytic activity of diaphorase.

Preferably, when ELISA sandwich immunoassays are performed, the buffer used to coat the solid support with the monoclonal or polyclonal antibody is a citrate buffer. Typically, the citrate buffer is at a concentration of from about 50 mM to about 150 mM. Preferably, the citrate buffer is at a concentration of from 75 mM to about 125 mM. More preferably, the citrate buffer is at a concentration of about 100 mM. Typically, the pH of the citrate buffer is from about pH 5 to about pH 7. Preferably, the pH of the citrate buffer is from about 5.5 to about 6.5. More preferably, the pH of the citrate buffer is about 6.0. A particularly preferred buffer is 0.1 M sodium citrate, pH 6.0.

Preferably, when ELISA sandwich immunoassays are performed, the enzyme label of the labeled anti-mycoplasmal antibody used for detection is alkaline phosphatase. However, as described above, other enzyme labels can alternatively be used.

Coating of the solid support with the unlabeled anti-mycoplasmal antibody is typically performed by methods known in the art. As disclosed above, a particularly preferred buffer for coating the solid support with the unlabeled anti-mycoplasmal antibody is 0.1 M sodium citrate, pH 6.0.

Before the performance of the ELISA sandwich immunoassay, the plates are washed to remove excess unbound antibodies. Typically, the plates are washed with a conventional washing buffer such as phosphate buffered saline. Typically, the plates are washed three to four times before the performance of the assay.

In the performance of the ELISA sandwich immunoassay, the size of the sample is typically from about 50 µL to about 150 µL. Preferably, the size of the sample is about 100 µL. The size of the sample will vary with the source of the sample and with the expected concentration of mycoplasmal antigen in the sample.

Accordingly, another aspect of the invention is a method for performing an ELISA assay method to detect one or more antigens characteristic of a mycoplasmal species, strain, or biotype as described above. The method, in general, comprises: (1) coating a solid support with a first, unlabeled, antibody specific for the antigen; (2) contacting the coated solid support with a sample that may contain the antigen to bind the antigen to the first unlabeled antibody bound to the solid support; (3) contacting the antigen bound to the antibody bound to the solid support with a second, labeled, antibody specific for the antigen; and (4) quantitating the second, labeled, antibody bound to the solid support in order to quantitate the antigen in the sample. The ELISA assay can be used to quantitate the antigens, to determine the efficacy of immunization, and for controlling immunization of waterfowl.

In another aspect of this invention, to produce an effective vaccine against the waterfowl *mycoplasmas*, such as 1220 type of *mycoplasma, M. anseris, M. anatis,* or *M. imitans*, the vaccine contains antigen derived from a biotype of these *mycoplasmas*. Examples of specific embodiments would include vaccines containing antigen derived from one or more different strains of waterfowl *mycoplasmas*. In a further specific embodiment, the vaccine comprises antigen derived from one or more than one strain of *mycoplasma*. In a further specific embodiment, the vaccine comprises antigen derived from one or more biotypes and antigen derived from another pathogen. In a further specific embodiment, the vaccine comprises inactivated biotype A, B or C. In a further specific embodiment, the vaccine comprises at least one inactivated biotype with antigen derived from another pathogen. In a preferred embodiment, the vaccine comprises an inactivated strain of waterfowl *mycoplasma*, such as 1220 type of *mycoplasma, M. anseris or M. imitans*, or the combination thereof, such as when mixed infection is present, as defined herein; in this embodiment, at least one biotype is present.

It is anticipated that additional strains of the waterfowl *mycoplasma* may emerge and may be isolated with continued animal production. Additional waterfowl *mycoplasmas* can be added to the vaccine as needed. It is a matter of routine practice to sample organs of ducks and geese to isolate the 1220 type of *Mycoplasma* or other waterfowl *mycoplasma* in cultures. Vaccines can be formulated based on the prevalence of strains or biotypes of strains present in the environment. Autogenous vaccines, i.e. those vaccines for use on the farm where the microorganisms are isolated, can be custom-designed to contain all strains found on the farm, but not any other strains of waterfowl *mycoplasmas*. Vaccines developed for use by a mass market, i.e. those vaccines produced for general use on many different farms containing preselected strains, can also be developed, marketed and used.

In another aspect, this invention provides a vaccine comprising a single, inactivated waterfowl *mycoplasma* such as the 1220 type of *Mycoplasma* biotype or strain, *M. anseris, M. anatis* or *M. imitans* in a pharmaceutically acceptable excipient, and a suitable adjuvant. In a specific embodiment, the vaccine contains inactivated strains of these *mycoplasmas* or any mixture thereof and may further contain antigens from other pathogens.

In a preferred embodiment, the inactivated vaccines of this invention are produced from biotypes freshly isolated from infected animals or from cryopreserved biotype cultures freshly prepared from infected animals. In a preferred embodiment, the attenuated vaccines of this invention are produced from cultures of biotypes, which have been treated so as lost ability to replicate within the vaccinated animal.

The inactivated waterfowl *mycoplasma*(s) may be further processed to fractionate and/or standardize the antigenic mass. For example, specific strains might be isolated from samples and combined to form specific combinations of strains in specific ratios. Similarly, components from a specific inactivated waterfowl *mycoplasma* biotype might be fractionated and a subset of those fractions combined with similarly fractionated components of another strain to standardize the antigenic component of the vaccine preparation and to optimize its efficacy. In one embodiment, the antigenic components derived from a single strain. In another embodiment, the vaccine preparations are standardized to provide a required minimum cell content per formulated dose. In one preferred embodiment, the vaccine comprising inactivated waterfowl *mycoplasma* (s) is formulated to deliver at least $1\times10^5$ cfu/ml cell equivalents of one or more strains per dose. In another preferred embodiment, the vaccine comprising inactivated waterfowl *mycoplasma* (s) is formulated to deliver at least $1\times10^6$ cfu/ml cell equivalents of one or more strains per dose. However, higher doses can be used, such as $10^8$ or $10^9$ cfu per unit dose in some circumstances and are within the scope of the invention. A complete vaccination of a waterfowl species comprises the administration of recommended doses. In a preferred embodiment, one such dose will be administered. In a further preferred embodiment, two such doses will be administered. It is understood by those skilled in the art that the critical value in describing a vaccination dose is the total amount of immunogen needed to elicit a protective response by the host animal to infectious disease caused by virulent or wild-waterfowl *mycoplasma*. The number and volume of doses used can be varied and are determined by the practitioner based on costs and the need to avoid deleterious side effects in the animal caused by the administration of the vaccine. For example, the volume of one administration typically does not exceed 1.0 milliliter, but can be greater in some circumstances. Dosage for goslings or ducklings can be smaller, such as 0.1 to 0.5 milliliter. The number of doses of inactivated vaccine needed in adult animals is typically one initial dose followed by one additional dose and annual revaccination. In addition, the number of cfu administered per dose can be varied depending on the size of the waterfowl to which the injections are administered, the state of their health, and other factors known in the art. In some cases, the cfu administered per dose can be increased, to as much as $10^8$ or $10^9$ cfu per unit dose.

The vaccines of the present invention may further comprise antigenic material of other viruses and/or microorganisms known to be duck and goose pathogens, including, but not limited to, inactivated viruses or microorganisms. Such combination vaccines provide protection against a plurality of diseases to which the waterfowl species are exposed, including but not limited to immunogenic compositions for *Staphylococcus aureus, Pasteurella haemolytica, Pasteurella multocida, Escherichia coli, Salmonella, Rimerella antipestifer, Chlamydophila, Erysipelothrix rhusiopathiae, Listeria monocytogenes*, goose parvovirus, reticuloendotheliosis virus, duck enteritis virus, circovirus and other pathogens known in the art. Therefore, in one alternative, the vaccine can further comprise an inactivated non-mycoplasmal microorganism or an antigen from a non-mycoplasmal microorganism. The non-mycoplasmal microorganism can be selected from the group consisting of *Staphylococcus aureus, Pasteurella haemolytica, Pasteurella multocida, Escherichia coli, Salmonella, Rimerella antipestifer, Chlamydophila, Erysipelothrix rhusiopathiae, Listeria monocytogenes*, goose parvovirus, reticuloendotheliosis virus, duck enteritis virus, and circovirus. Other non-mycoplasmal microorganisms can also be used.

In other embodiments, the vaccine of this invention further comprises a suitable adjuvant. As used herein, an "adjuvant" is a potentiator or enhancer of the immune response. The term "suitable" is meant to include any substance, which can be used in combination with the vaccine immunogen (i.e., 1220 type of *mycoplasma* strains or fractions thereof) to augment the immune response, without producing adverse reactions in the vaccinated animal. Effective amounts of a specific adjuvant may be readily determined so as to optimize the potentiation effect of the adjuvant on the immune response of an animal vaccinated. In specific embodiments, suitable adjuvants can be chosen from the following group: mineral, vegetable or fish oil with water emulsions, incomplete Freund's adjuvant, *E. coli* J5, dextran sulfate, iron oxide, sodium alginate, Bacto-Adjuvant, certain synthetic polymers such as CARBOPOL® (polyacrylic acid) (BF Goodrich Company, Cleveland, Ohio), especially CARBOPOL® (polyacrylic acid) 941, described in U.S. Pat. No. 5,565,205 to Petersen et al., incorporated herein by this reference, poly-amino acids and co-polymers of amino acids, saponin, carrageenan, an emulsion of mycobacterial cell wall fractions comprising trehalose dimycolate and muramyl dipeptide, such as REGRESSIN (Vetrepharm, Athens, Ga.), N,N-dioctadecyl-N',N'-bis (2-hydroxyethyl)-propanediamine, such as AVRIDINE, long chain polydispersed β(1,4)-linked mannan polymers interspersed with O-acetylated groups (e.g. ACEMANNAN), deproteinized highly purified cell wall extracts derived from a non-pathogenic strain of *Mycobacterium* species (e.g. EQUIMUNE, Vetrepharm Research Inc., Athens Ga.), mannide monooleate, paraffin oil, muramyl dipeptide, aluminum hydroxide and aluminum phosphate. REGRESSIN is described in S. A. Vézina & D. Archambault, "Modulatory Effect of *Mycobacterium* Cell Wall Extract (Regressin) on Lymphocyte Blastogenic Activity and Macrophage Cytokine Gene Transcription in Swine," *Clin. Diagn. Lab. Immunol.* 4: 314-320 (1997), incorporated herein by this reference.

Other adjuvants are known in the art and are described in F. R. Vogel, "Immunologic Adjuvants for Modern Vaccine Formulations," *Ann. N.Y. Acad. Sci.* 754: 153-160 (1995), incorporated herein by this reference. Such additional adjuvants include, but are not limited to: squalene; virosomes; QS-21, which contains soluble triterpene glycoside saponins; MF59, which contains squalene; aluminum hydroxide gel plus killed Bordetella pertussis; and immune stimulatory complexes (ISCOMs), which are spherical open cage-like structures, typically about 40 nm in diameter, and include cholesterol, phospholipids, and Quillaia saponins. ISCOMs are described in M. Chen et al., "Vaccination with Recombinant Alphavirus or Immune-Stimulating Complex Antigen Against Respiratory Syncytial Virus," *J. Immunol.* 169: 3208-3216 (2002), incorporated herein by this reference.

Still other adjuvants are known in the art, including DEAE dextran, disclosed in U.S. Pat. No. 5,338,543 to Fitzgerald et al., incorporated herein by this reference, *Escherichia coli* heat-labile toxin (LT) or cholera toxin, disclosed in U.S. Pat. No. 6,001,348 to Witvliet, incorporated herein by this reference, adjuvants that include a lecithin, an oil, and an amphiphilic surfactant and that are capable of forming a stable oil-in-water emulsion, described in U.S. Pat. No. 6,814,971 to Roberts et al., incorporated herein by this reference, and marketed as AMPHIGEN, cationic lipids such as DMRIE and DOPE, described in U.S. Pat. No. 7,691,368 to Parisot et al., incorporated herein by this reference.

In addition, the composition can include a co-adjuvant, as described in U.S. Pat. No. 7,608,279 to Parisot et al., incorporated herein by this reference, such as CpG oligonucleotides (ODN), including ODN 2006, 2007, 2059, or 2135, poly A-poly U, dimethyldioctadecylammonium bromide (DDA), and chitosan.

In addition, in another alternative, the composition can include a microparticulate carrier, such as a polysaccharide. Typically, the polysaccharide is agarose. Typically, the microparticulate carrier, such as agarose, comprises particles less than about 10 μm in diameter; preferably, the microparticulate carrier comprises particles less than about 5 μm in diameter. Agarose is a natural polysaccharide, a D-galactose polymer that is biodegradable and is compatible with avian cells. The composition can further include at least one molecule that can modulate immune pathways such as a pathogen associated molecular pattern (PAMP) selected from the group consisting of a TLR 1 receptor agonist, a TLR 2 receptor agonist, a TLR 3 receptor agonist, a TLR 4 receptor agonist, a TLR 5 receptor agonist, a TLR 6 receptor agonist, a TLR 7 receptor agonist, a TLR 8 receptor agonist, a TLR 9 receptor agonist, a NOD-1 agonist, a NOD-2 agonist, an agonist for DC-SIGN, an agonist for L-SIGN, an agonist for a mannose receptor, and an agonist or antagonist molecule of a kinase involved in a PAMP recognition pathway.

When a microparticulate carrier is used, the antigen or antigens and the pathogen associated molecular pattern (PAMP) can be non-covalently or covalently attached to the microparticles. Methods for covalent attachment are known in the art and are described for example, in P. Tijssen, "Practice and Theory of Enzyme Immunoassays" (Elsevier, Amsterdam, 1985, pp. 283-289, in S. S. Wong, "Chemistry of Protein Conjugation and Crosslinking" (CRC Press, Boca Raton, Fla., 1993), in T. E. Creighton, ed., "Protein Function: A Practical Approach" (IRL Press, Oxford, 1989), and in G. T. Hermanson, "Bioconjugate Techniques" (Academic Press, San Diego, 1996), all of which are incorporated herein by reference. Typically, when the microparticles are agarose, the bioactive molecule is attached to a hydroxyl group of the agarose. In general, the hydroxyl residues of polysaccharides can be activated by certain compounds that form intermediate reactive derivatives containing good leaving groups for subsequent nucleophilic substitution. Reaction of these activated hydroxyls with nucleophiles such as amines (for example, lysine groups in proteins or peptides) results in stable covalent bonds that crosslink the bioactive molecule to the agarose. Suitable reagents include carbonyldiimidazole, chloroformate derivatives, tresyl chloride, tosyl chloride, cyanogen bromide, divinylsulfone, cyanuric chloride, and bis-epoxides. Alternatively, the hydroxyl groups of carbohydrates such as agarose can be modified with chloroacetic acid to create a carboxylate functional group. As another alternative, amine functional groups can be created on polysaccharides; the reducing ends of carbohydrate molecules or generated aldehydes can be reacted with diamine compounds of low chain length (i.e., typically less than about 6 carbon atoms in the chain) to yield short alkylamine spacers that can be used for subsequent conjugation reactions. Hydrazide groups can be similarly created using bis-hydrazide compounds. The resulting functional group can then be coupled to the bioactive molecule using various reactions. For example, if carboxyl groups are generated, they can then be conjugated to proteins or peptides via the mixed anhydride method, the carbodiimide method, using dicyclohexylcarbodiimide, and the Nhydroxysuccinimide ester method. Aliphatic amines can be conjugated to proteins or peptides by various methods, including carbodiimide, tolylene-2,4-diisocyanate, or maleimide compounds, particularly the N-hydroxysuccinimide esters of maleimide derivatives. An example of such a compound is 4-(N-maleimidomethyl)-cyclohexane-1-carboxylic acid. Another example is m-maleimidobenzoyl-N-hydroxysuccinimide ester. Still another reagent that can be used is N-succinimidyl-3-(2-pyridyldithio) propionate. Also, bifunctional esters, such as dimethylpimelimidate, dimethyladipimidate, or dimethylsuberimidate, can be used to couple amino-group-containing moieties to proteins. Other methods for covalent linkage of compounds, including peptides, proteins, and carbohydrates, as well as other compounds, to solid supports are known in the art. Methods for noncovalent attachment depend on multiple noncovalent interactions such as hydrogen bonds, hydrophobic bonds, and salt linkages that can stabilize the interaction.

Suitable microparticulate carriers, including agarose, PAMPs, and conjugation methods are described in PCT Patent Application Publication No. WO 2006/081576 by Szathmary et al., incorporated herein by this reference.

Typically, the vaccine is protective of disease in a species of goose or duck following systemic administration. In one alternative, the vaccine provides immunity after a single administration in the waterfowl against mycoplasmas capable of causing disease in the waterfowl. In another alternative, the vaccine provides immunity after repeated administration in the waterfowl against mycoplasmas capable of causing disease in the waterfowl.

Typically, the vaccine provides a serological response after a single administration in the waterfowl against mycoplasmas capable of causing disease in the waterfowl. Typically, the serological response is detectable by an ELISA test. The ELISA test can be used for detecting natural mycoplasmal infection and for controlling immunization of waterfowl.

In one alternative, the mycoplasmal strain for use in the vaccine can be isolated from a specific farm to provide a farm-specific vaccine.

In one alternative, the vaccine is for use in a flock of waterfowl being treated with medication prior to or during vaccination. The medication can be at least one antibiotic, although other medications can alternatively be used.

Particular examples of a vaccine according to the present invention include: (1) a vaccine comprising inactivated *Mycoplasma* sp. strain 1220, *Mycoplasma anatis*, and *Mycoplasma anseris*, each at $10^6$ cfu with incomplete Freund's adjuvant in a total volume of 0.1 to 1 mL per unit dose; (2) a vaccine comprising inactivated *Mycoplasma anseris* at $10^6$ cfu with incomplete Freund's adjuvant in a total volume of 0.1 to 1 mL per unit dose; (3) a vaccine comprising inactivated *Mycoplasma* sp. strain 1220 at $10^6$ cfu with incomplete Freund's adjuvant in a total volume of 0.1 to 1 mL per unit dose; (4) a vaccine comprising inactivated *Mycoplasma anatis*, *Mycoplasma anseris*, and *Mycoplasma imitans* each at $10^5$ cfu with incomplete Freund's adjuvant in a total volume of 0.1 to 1 mL per unit dose; (5) a vaccine comprising inactivated *Mycoplasma anatis* at $10^5$ cfu with incomplete Freund's adjuvant in a total volume of 0.1 to 1 mL per unit dose; (6) a vaccine comprising inactivated *Mycoplasma* sp. strain 1220 and *Mycoplasma imitans* each at $10^6$ cfu with incomplete Freund's adjuvant in a total volume of 0.1 to 1 mL per unit dose; (7) a vaccine comprising inactivated *Mycoplasma cloacale* and *Mycoplasma anatis* each at $10^6$ cfu and killed *Escherichia coli* bacteria at $10^5$ cfu with incomplete Freund's adjuvant in a total volume of 0.1 to 1 mL per unit dose; (8) a vaccine comprising comprises inactivated *Mycoplasma anatis* and *Acholeplasma axantum* each at $10^6$ cfu with incomplete Freund's adjuvant in a total volume of 0.1 to 1 mL per unit dose; and (9) a vaccine comprising inactivated *Mycoplasma* sp. strain 1220 and *Mycoplasma cloacale* each at $10^6$ cfu with incomplete Freund's adjuvant in a total volume of 0.1 to 1 mL per unit dose. Other vaccines according to the general principles described herein are within the scope of the present invention. The doses and cfu per dose can be adjusted as described above according to the size, weight, and general health of the waterfowl to which the vaccine is to be administered.

In another aspect, this invention discloses a method for immunizing a waterfowl against infectious disease caused by a waterfowl *mycoplasma* comprising administering to a bird immunogenic amounts of the *mycoplasma* strain(s) to elicit a protective immune response in the bird. Preferably, the method comprises administering a vaccine comprising antigen from at least one inactivated strain to elicit a protective immune response by the bird. Preferably, the method comprises administering the vaccine of the present invention as described above. Immunization may be performed subcutaneously or via other routes. Repeated doses of the vaccine preparations, i.e. "boosters," are preferable at periodic time intervals to enhance the immune response initially or after a long period of time since the last dose. The time interval between vaccinations varies depending on the age and condition of the animal. For adult animals, the first vaccination is preferably given at the beginning of laying period followed by a "booster" dose 2 weeks later, and preferably followed by a repeated immunization before each laying period. Goslings and young ducks are preferably vaccinated at 7-8 weeks of age, followed by administration of a booster before first egg production period and annually thereafter.

In another embodiment of the methods of this invention, the multiple strains of waterfowl *mycoplasma*(s) comprising the vaccine can be delivered in separate administrations to the animal. For example, the vaccine comprising inactivated strains of waterfowl *mycoplasmas* can be delivered by separately administering an immunogenic amount of one waterfowl *mycoplasma*, such as type 1220 *mycoplasma* in one injection and an immunogenic amount of another waterfowl *mycoplasma* such as *M. anseris* in another injection. In a further embodiment, each separately administered strains can be administered as a combination vaccination, comprising antigenic material of other viruses and/or microorganisms known to be duck and goose pathogens.

The term "immunogenic amount" means an amount of an immunogen, i.e. the inactivated biotype(s) or a portion thereof, such as lipid, sugar, protein, lipoprotein, glycoprotein, DNA or peptide, which is sufficient to induce an immune response in a vaccinated waterfowl species and which protects the animal against disease caused by wild-type or virulent waterfowl *mycoplasma* infections upon exposure thereto or which has a commercially beneficial effect that lessens the effect of the waterfowl *mycoplasma* infection weight gain or animal health. In a preferred embodiment, ducks and geese are immunized by administering at least approximately $10\times10^5$ cells of 1220 type of *mycoplasma* cell equivalents of each inactivated strain in the vaccine. In a specific embodiment, animals are immunized by administering at least approximately $1\times10^5$ waterfowl *mycoplasma* strain, such as *M. anseris* cell equivalents and approximately $1\times10^5$ cells of 1220 type of *mycoplasma* cell equivalents, which have been inactivated, in at least two injections. In another specific embodiment, the bird animals are immunized by administering at least approximately $1\times10^5$ cells of 1220 type of *mycoplasma* cell equivalents, $1\times10^5$ cells of *M. anatis* cell equivalents and approximately $1\times10^5$ cells of *M. anseris* cell equivalents, which have been inactivated, in at least two injections.

In a preferred method, selected waterfowl *mycoplasma*(s) are grown separately as pure cultures, free of contamination by viruses, bacteria or any other microbial agent, including other biotypes of waterfowl *mycoplasma* to the desired cell equivalents, inactivated as described herein, and then combined in equal amounts with a pharmaceutically acceptable excipient to produce a waterfowl *mycoplasma* vaccine. Alternatively, the strains can be grown together as a mixed culture to the desired cell equivalents, inactivated and then, optionally, combined with a pharmaceutically acceptable excipient and a suitable adjuvant to produce a waterfowl *mycoplasma* vaccine.

In a further embodiment of the hereinabove disclosed method of producing a waterfowl *mycoplasma* vaccine, the inactivated *mycoplasma* are mixed with a suitable adjuvant. In a preferred method, the suitable adjuvant is an oil emulsion or molecule(s) that activate protective immunity.

Selected waterfowl *mycoplasmas* may be used as the basis for diagnostic tools to detect the presence of waterfowl *mycoplasma*. In one aspect of this invention, samples from ducks and geese would be tested for the presence of antibodies specific for waterfowl *mycoplasma* by contacting the samples with given waterfowl *mycoplasma* cells or antigens derived from it. Examples of technologies that could be adapted to such a method include, but are not limited to, ELISA, hemagglutination inhibition (HI) and immunoblot. Examples of specific embodiments would include antigens derived from one or more waterfowl *mycoplasma* isolates. In a preferred embodiment, antigen from each of the isolates is to be utilized to test for the presence of antibodies specific for each of the waterfowl *mycoplasma* isolates or biotypes, thus allowing an autogenous vaccine to be administered. In another embodiment, antibodies raised against the waterfowl *mycoplasma* isolates or biotypes or antigens derived from selected isolates would be used to test for the presence of the waterfowl *mycoplasma*. Examples of specific embodiments would include antibodies reactive to antigens derived from one or more of the waterfowl *mycoplasma* strains (e.g. *M. anatis, M. anseris,* 1220 type of *mycoplasma, M. imitans*, or other *mycoplasma* strains). In another embodiment, antigens derived from different strains would be utilized to test for the presence of antibodies specific against antigens from a given strain.

In a further embodiment, the present invention provides an isolated 1220 type of *mycoplasma* or another waterfowl *mycoplasma* or any combination thereof.

Methods of Vaccinating an Animal

The present invention also includes methods of vaccinating a waterfowl against *mycoplasma* infection. The methods according to this aspect of the invention comprise administering to a waterfowl an immunologically-effective amount of a vaccine composition comprising a *mycoplasma* antigen of the invention. As used herein, the expression "*mycoplasma* antigen of the invention" encompasses *mycoplasma* antigen from selected strains that are described and/or claimed elsewhere herein. The expression "immunologically-effective amount" means that amount of vaccine composition required to invoke the production of protective levels of antibodies in an animal upon vaccination. The vaccine composition may be administered to the animal via different routes, such as subcutaneously, mucosally, intravenously, intramuscularly, or other routes known in the art.

The animal to which vaccine is administered is preferably a goose or duck; other animals can also be immunized. Typically, the vaccine formulations of the invention are administered in a manner such that the formulations are immediately or eventually brought into contact with the immune system of birds.

Typically, in methods of immunization according to the present invention, the method comprises a method of immunizing a waterfowl against infectious disease comprising administering to a bird an immunogenic amount of at least one mycoplasmal strain to elicit a protective immune response in the bird. Typically, the method comprises administering a vaccine comprising at least one inactivated strain to elicit a protective immune response in the bird.

In these methods, the vaccine can comprise at least one pharmaceutically acceptable excipient or at least one pharmaceutically acceptable adjuvant. Suitable excipients and adjuvants are described above.

The inactivated waterfowl mycoplasmal strain can be, for example, *Mycoplasma* sp. strain 1220, *Mycoplasma anseris, Mycoplasma anatis, Mycoplasma cloacale, Mycoplasma imitans, Mycoplasma gallisepticum, Mycoplasma synoviae, Acholeplasma modicum*, and *Acholeplasma axantum*. Other inactivated waterfowl mycoplasmal strains can be used. As described above, two or more, or three or more, inactivated waterfowl mycoplasmal strains can be used; when two or more, or three or more, inactivated waterfowl mycoplasmal strains are used, one of the strains can be *Mycoplasma* sp. strain 1220.

Typically, when an adjuvant is used, the adjuvant is selected from the group consisting of: an oil; an aluminum hydroxide-oil emulsion; a mineral oil-water emulsion; a vegetable oil-water emulsion; a fish oil-water emulsion, a water-oil-emulsion; incomplete Freund's adjuvant; *Escherichia coli* J5, dextran sulfate; iron oxide; sodium alginate; a synthetic polymer; CARBOPOL® (polyacrylic acid); a polyamino acid; a copolymer of two or more amino acids; saponin; carrageenan; an emulsion of mycobacterial cell wall fractions comprising trehalose dimycolate and muramyl dipeptide; N,N-dioctadecyl-N',N'-bis(2-hydroxyethyl)propanediamine; a long-chain polydisperse β(1,4)-linked mannan polymer interspersed with O-acetylated groups; a deproteinized cell wall extract from a non-pathogenic strain of *Mycobacterium*; mannide monooleate; paraffin oil; muramyl dipeptide β-propiolactone; aluminum hydroxide; and aluminum phosphate, as described above. Other adjuvants known in the art can be used.

Typically, the mycoplasmal strain is inactivated by an inactivating agent or method selected from the group consisting of: formalin, azide, freeze-thaw, sonication, heat treatment, sudden pressure drop, detergent, lysozyme, phenol, proteolytic enzymes, β-propiolactone, thimerosal, and binary ethyleneimine, as described above. Particularly preferred inactivating agents or methods include β-propiolactone and formalin.

In a method according to the present invention, the vaccine can further comprise an inactivated non-mycoplasmal microorganism or an antigen from a non-mycoplasmal microorganism. The non-mycoplasmal microorganism can be selected from the group consisting of *Staphylococcus aureus, Pasteurella haemolytica, Pasteurella multocida, Escherichia coli, Salmonella, Rimerella antipestifer, Chlamydophila, Erysipelothrix rhusiopathiae, Listeria monocytogenes*, goose parvovirus, reticuloendotheliosis virus, duck enteritis virus, and circovirus.

Typically, in a method of vaccination according to the present invention, the result of vaccination is such that the incidence of disease caused by waterfowl *mycoplasma* in a flock to which the vaccine is administered is greater before vaccination than after vaccination. Typically, in a method of vaccination according to the present invention, vaccination of breeding waterfowl prevents at least one deleterious effect caused by mycoplasmal infection selected from the group consisting of: (1) reduction of body weight; (2) development of pathological lesions of respiratory and reproductive organs; and (3) colonization of organs of birds induced by *mycoplasma* infection. In one alternative, the deleterious effect caused by mycoplasmal infection and prevented by vaccination is the development of pathological lesions of respiratory and reproductive organs and the pathological lesions of reproductive organs are salpingitis and inflammation of the phallus.

Typically, in a method of vaccination according to the present invention, vaccination of breeding waterfowl reduces mycoplasmal infection of birds and embryos and normalizes egg production that would otherwise be reduced by mycoplasmal infection. Typically, in a method of vaccination according to the present invention, vaccination of breeding waterfowl increases maternal immunity of goslings originating from immunized breeders. Typically, in a method of vaccination according to the present invention, vaccination of breeding waterfowl reduces egg infertility caused by mycoplasmal infection. Typically, in a method of vaccination according to the present invention, vaccination of breeding waterfowl increases weight gains and reduces mortality of goslings originating from immunized breeders. Typically, in a method of vaccination according to the present invention, the vaccine is administered to young animals and increases their immunity against mycoplasmal infection.

A method of vaccination according to the present invention can further comprise the step of co-administering at least one additional *mycoplasma*. The additional *mycoplasma* can be selected from the group consisting of *Mycoplasma* sp. strain 1220, *Mycoplasma anseris, Mycoplasma anatis, Mycoplasma cloacale, Mycoplasma imitans, Mycoplasma gallisepticum, Mycoplasma synoviae, Acholeplasma modicum*, and *Acholeplasma axantum*. Similarly, a method of vaccination according to the present invention can further comprise the step of co-administering at least one additional bacterin. The additional bacterin can be selected from the group consisting of *Staphylococcus aureus, Pasteurella haemolytica, Pasteurella multocida, Escherichia coli, Salmonella, Rimerella antipestifer, Chlamydophila, Erysipelothrix rhusiopathiae, Listeria monocytogenes*, and *Chlamydophila psittaci*. Also similarly, a method of vaccination according to the present invention can further comprise step of co-administering at least one live or inactivated virus. The live or inactivated virus can be selected from the group consisting of goose parvovirus, influenza virus, poliovirus, enteritis virus, circovirus, West Nile virus, hepatitis virus, and reticuloendotheliosis virus. A particularly preferred virus for co-administration is goose parvovirus.

The invention is illustrated by the following Examples. These Examples are included for illustrative purposes only, and are not intended to limit the invention.

Example 1

Protection by *Mycoplasma* Vaccine Against Reduction of Body Weights, Pathological Lesions, and Colonization of Organs of Birds with *Mycoplasma* Caused by Mycoplasmal Infection in Geese and Ducks In this experiment 20 two-year-old geese were divided into 2 groups (10 birds per group) that way that individual body weights were measured and average body weights of the groups did not differ from each other. Group 1 was immunized with 1 ml of the vaccine containing killed inactivated type 1220 *mycoplasma, M. anatis* and *M. anseris* at $10^6$ cfu formulated with an incomplete Freund's adjuvant. Vaccine was administered in right site of lower part of the neck subcutaneously as in experiment 1. Group 2 was inoculated with PBS subcutaneously on the right side of the lower part of the neck on the same day and way as the Group 1. Three weeks later all birds were challenged with virulent *mycoplasma* in the left thoracic air sac. Before challenge and at the end of experimental period individual body weights of geese were measured and the average body weights of groups were compared by Student's t-test as in experiment 1. At the end of study the geese were necropsied and examined for pathological lesions. Beside this histological examination of lung was performed for detecting presence of interstitial pneumonia, lymphoid phalluses and catarrhal pneumonia. In case of interstitial pneumonia scores were following: score 0=no lesions, 1=accumulation of few lymphocytes around bronchioli and interstitial septum, 2=presence of more lymphocytes, 3=significant amount of lymphocytes around bronchioli blood vessels and interstitial septum. Lymphoid follicles, score 0=no follicles, 1=few, 2=medium number, 3=a lot of lymphoid follicles were found in serous membrane of bronchi and bronchioli. Catarrhal pneumonia; score 0= no exudates and cells in bronchioli, 1=accumulation of a small amount, 2=medium amount and 3=a big amount of exudates, epithelial cells and neutrophils in lumen of bronchi and alveoli.

Swabs from thoracic air sacs, cut surface of the lung, liver and spleen were streaked on *mycoplasma* agar plate in order to re-isolate the challenge strains. After five days of incubation of agar plates, colonies of mycoplasmas obtained from each all organs were examined by epifluorescence test using fluorescein isocyanine labeled hyperimmune sera prepared against challenged stain.

Results

In this experiment the average body weight of non-immunized challenged group has decreased statistically significantly (by 11%) in comparison with by weight measured before challenge. At the same time in the group vaccinated with vaccine and challenged, the body weight increased. Similarly to the results of the experiment the vaccine has induced immunity against challenged, since lesion scores of left and right thoracic air sacs and abdominal air sacs in the vaccinated group remained low (6) while those in non-immunized challenged group significantly higher (34). Similar results were observed scores of histological lesions of lung (5) in vaccinated group in comparison with those of non-vaccinated and challenged group (42).

Immunization of geese significantly reduced isolation rates from air sac. Immunization also protected the geese against colonization of lung, liver, spleen and kidney with *mycoplasmas* (2) in contract to the non-vaccinated challenged group where 28 organs were colonized with *mycoplasma*. The vaccine induced a serological response against *M. anseris, M. anatis* and type 1220 *mycoplasma* as measured by ELISA.

Example 2

Effect of Vaccination on Mycoplasmal Infection, Egg Production, and Serological Response of Birds At the farm "S" 3 flocks were available. Flock No. 1 consisted of 837 layers in second year of egg production was immunized with the Vaccine No. 2. Containing strain of *M. anseris*. The flock No. 2 consisted of 516 geese was immunized with the Vaccine No. 3 containing strain of 1200 type of *mycoplasma*. The flock No. 3 consisting of 1205 layers was left without immunization. Proportion of females and ganders was 4:1. These flocks were kept in different buildings but their equipment was the same. The farm was equipped with an "ad libitum" system of feed and water supply. Feed was the same in all flocks without medication. Egg production started in first part of January and prolonged till the end of May.

The flocks were tested for *mycoplasma* carrying. Before vaccination and two month after immunization of flocks trachea swabs were collected from 40 birds in each flock. Swabs were streaked on the surface of *mycoplasma* agar medium B. After 7 days of incubation at 37° C. two colonies were picked up from each sample and transferred into fluid medium. Isolates were identified by growth inhibition and epifluorescence tests using hyperimmune sera prepared against the strain *Mycoplasma* sp. 1220 and *M. anseris*.

Results

Before vaccination *mycoplasma* isolation rates from trachea swabs were very high: 95.0-100%. After application of Vaccines No. 2 and No. 3 *mycoplasma* isolation rates decreased to 20.0%. *Mycoplasma* isolation rate remained high in the non-vaccinated flock.

In the flock immunized with the vaccine No. 2, an average of 43.88 eggs/breeder was obtained. In the flock immunized with the Vaccine No. 3, an average of 48.60 eggs/breeder was found. At the same time in the non-immunized flock, an average of only 32.2 eggs/breeder was recorded.

Serological testing revealed that before vaccination the seropositivity was low, 10.0-15.0%. After vaccination seropositivity rate increased depending on the vaccine used (60.0% for *M. anseris* and 80.0% for *Mycoplasma* sp. 1220 type of strain). The highest percentage of positive geese was recorded in the flock No. 2 vaccinated with Vaccine No. 3. In the non-immunized flock the seropositivity remained low.

Example 3

Testing Maternal Immunity of Goslings Originating from Vaccinated Goose Breeders One group of 800 layers was immunized with the *mycoplasma* vaccine (containing killed inactivated *M. anatis* and *M. anseris* and *M. imitans* $10^5$ cfu with incomplete Freund's adjuvant) another group of 1200 layers left without immunization. The proportion of females and ganders was 4:1. These flocks were kept in different buildings but their equipment was the same. The farm was equipped with an "ad libitum" system of feed and water supply. Feed was the same in all flocks without medication. Egg production started in first part of January and prolonged till the end of May.

In age of 1 day and 5 weeks 20 goslings were collected from offspring geese originated from vaccinated layer flocks. Similarly 20 of one day-old and 20 of 5 weeks old goslings originated from non-vaccinated layers were taken for control. All goslings were tested for antibodies against *mycoplasma* included in the vaccine. Body weight of gosling was measures in each group then goslings were challenged with 1.0 ml of the 48 hours old broth culture of wild-type *M. anatis* and *M. anseris* and *M. imitans* ($7.3 \times 10^7$ CFU/ml). Two weeks post challenge body weight gains of goslings were measured again and compared by Student's t-test. Afterwards the goslings were necropsied and examined for pathological lesions. Sum of lesions scores of groups of the same age were compared by Chi-square test.

Results

Body weights of newly hatched goslings originated from vaccinated flocks had statistically significantly higher body weights (208.7 g) than those goslings originated from non-vaccinated flocks (195.0 g). The vaccinated animals showed a serological response to the vaccine strains, whereas the control animals had low serological response.

On the day 10 post-challenge, average body weight gains of goslings of originated from vaccinated breeder layers showed significantly higher values (288.4 g) than goslings coming from non-vaccinated breeders (199.0 g).

Due to challenge severe air sac lesions with very high lesion scores were recorded in all control groups of goslings (82/20) originated from non-vaccinated flocks. At the same time only mild lesions with low lesion scores were detected in goslings (19/20) hatched from eggs of vaccinated flocks. The isolation rate of *mycoplasmas* from organs of challenged goslings originated from vaccinated flocks was significantly reduced in comparison with control goslings.

Body weights of 5 weeks old goslings originated from vaccinated flocks had statistically significantly higher body weights (1468.0 g) than those goslings originated from non-vaccinated flocks (1187.0 g).

On day 10 post-challenge, average body weight gains of goslings of originated from vaccinated breeder layers showed significantly higher values (400.2 g) than goslings coming from non-vaccinated breeders (132.0 g).

Due to challenge severe air sac lesions with very high lesion scores were recorded in all control groups of goslings (89/20) originated from non-vaccinated flocks. At the same time only mild lesions with low lesion scores were detected in goslings (13/20) hatched from eggs of vaccinated flocks. The isolation rates of *mycoplasmas* from organs of challenged goslings originated from vaccinated flocks were significantly reduced in comparison with control goslings.

Example 4

Testing of Vaccine for Preventing Egg Infertility of Geese and Ducks

Eleven flocks had been infected with *mycoplasma* by mixing geese from a very infected flock. In consequence a high incidence of egg infertility occurred. To reduce infertility of eggs it was decided to vaccinate 10 flocks with *mycoplasma* vaccine containing killed and inactivated *M. anatis* strain ($10^5$ cfu) with incomplete Freund's adjuvant. One flock (6/1) was left without vaccination as control.

The percentage of mortality of geese, the number of eggs/goose layers, the percentage of infertile eggs, and hatchability were recorded in all 11 affected flocks before and after receiving geese from the flock affected flock and after vaccination.

Results

The dead animals and the slaughtered geese due to the infection with *mycoplasma* showed severe catarrhal-fibrinous airsacculitis, peritonitis and salpingitis. Ganders had phalluses with accumulation of fibrinous masses in genital organs.

In all affected 11 flocks isolation rates of *mycoplasmas* was very high: from cloaca 77.0-100%, from phallus lymph of ganders 33.3-100%, from lung 23.3-86.0%, from liver 10.0-56.7%, spleen 6.7-56.7%, from testicles 10.0-70.0%, from oviduct 50.0-90.0%, from ovaries 60.0-90.0%, from infertile eggs 50.0-90.0%. In contrary to above mentioned data isolation rates of *mycoplasma* from cloaca samples taken from control flocks was 5-15%. Serological examination of geese confirmed *mycoplasma* infection of tested flocks.

The egg production of immunized flocks (5/1, 5/2, 5/3 and 6/2) started at the beginning of January, while that of other flocks it started one month later. The percentage of infertile eggs in all vaccinated flocks varied very much but no case was recorded when the proportion of infertile eggs was higher than 20%. To the contrary in the affected not immunized flock 6/1 in second month of egg production, the proportion of infertile eggs proved to be significantly higher than 20%; in second part of March it was already 56.2-82.5% and in the last part of the egg production period it was recorded 85.9-96.9%. At the same time the percentage of culling had normalized to level of 0.5-1.0%, of mortality of geese to 5.7-7.5%, the percentage of hatchability to 23.9-27.5%, and the number of eggs to the level of 22.8-27.5 eggs/breeder.

Example 5

Effect of the Vaccination of Goose Breeders on Mortality and Body Weight of Offspring Goslings Goose breeders were vaccinated with a vaccine containing several killed and inactivated waterfowl *mycoplasma* strains isolated from the farm adjuvanted with a bacterial product-based adjuvant (LPS and bacterial cell wall extract). From the vaccinated flocks altogether 42,730 one-day-old goslings were sold to 13 different farms. The number of offspring goslings sold to these farms varied from 1,200 to 9,000. In the same period 75,250 goslings hatched from non-vaccinated flock were sold to 19 farms. The size of these gosling groups varied between 1,000 and 8,000.

Results

In these flocks originated from vaccinated breeders the average mortality rate was 6.86%. The average body weight of the geese was 5.66 kg and the raising period was 22.46 weeks.

In flocks originated from non-vaccinated breeders, the average mortality rate was 15.16%. In individual flocks, mortality ranged between 5 and 24.48%. The mortality rate for vaccinated flocks, (8.3% difference), was statistically significantly lower ($P<0.001$) than for flocks non-vaccinated breeders origin. The average body weight of these geese was 5.26 kg. The weight gain of 0.40 kg for vaccinated flocks was statistically significantly lower in comparison with control ones ($P<0.05$). The raising time for these control geese was 25.21 weeks. This raising period was longer by 2.75 weeks, a difference that was statistically significantly ($P<0.05$) and higher in comparison with those of goslings coming from vaccinated breeders. Analysis of the correlation between the number of geese in the flock and the mortality percentage showed a high coefficient of correlation ($r=0.85$) in offspring gosling of non-vaccinated flocks, while in the offspring goslings of vaccinated flocks, this coefficient was considerably lower ($r=0.39$). The higher is the number of geese in the flock, the higher is the mortality especially in flocks of origin from non-vaccinated breeders.

Example 6

Effect of Vaccination of Goose Breeders on Their Egg Production

For this study, Groups A and B of goose breeders (100 animals each) were used. Group A was vaccinated with a vaccine containing killed inactivated strain of type 1220 *mycoplasma* with an incomplete Freund's adjuvant and Group B was vaccinated with a vaccine containing killed inactivated strain of *M. anseris* with an incomplete Freund's adjuvant 4 and 2 weeks before the start of egg production. During the egg production period, we checked the number of eggs produced. As control, Group C was used, where no vaccination was performed.

Results

The animals in the immunized group gave a strong serological response to the type 1220 *mycoplasma* in Group A and *M. anseris* in Group B as measured by ELISA. In the immunized Group A on average 42.2 eggs/breeder was obtained. In the immunized Group B on an average 46.80 eggs/breeder was found. At the same time in the non-immunized Unit C flock, an average of only 30.0 eggs/breeder was recorded.

Example 7

Test of Efficacy of *Mycoplasma* Vaccine on 5-Week-Old Goslings

Sixty goslings of 5 week of age were distributed into 6 groups (10 birds in each group) in such a way that average body weights of groups did not differ from each other. Group 1 was immunized with 0.5 ml of the vaccine No. 1 (containing killed and inactivated *M. imitans* and type 1220 *mycoplasma* (both $10^6$ cfu) combined with a mineral oil adjuvant (incomplete Freund's adjuvant)). Group 2 was immunized with 0.5 ml of the vaccine No. 2 (containing killed and inactivated *M. cloacale* and *M. anatis* both $10^6$ cfu and *E. coli* ($10^5$ cfu) combined with a mineral oil adjuvant (incomplete Freund's adjuvant)). Group 3 was immunized with vaccine No. 3 containing killed and inactivated *M. anatis* and *A. axantum* (both $10^6$ cfu) combined with a mineral oil adjuvant (incomplete Freund's adjuvant)). Group 4 was immunized with the vaccine No. 4 containing killed and inactivated *M. cloacale* and type 1220 *mycoplasma* (both $10^6$ cfu) combined with a mineral oil adjuvant (incomplete Freund's adjuvant)). Group 5 was not immunized. After three weeks the birds of groups 1, 2, 3, 4 and 5 were challenged in the left thoracic air sac with 1.0 ml of 48 hours old mixture of the strains in the vaccine ($6.8 \times 10^8$ CFU/ml). Group 6 was not immunized and not challenged, left as a negative control. Body weights of goslings were measured individually before the start of the experiment and on day 14 post-challenge when all birds were sacrificed and examined for presence of pathological lesions of air sacs, *mycoplasmas* in inoculated air sacs, lung, liver and spleen.

Before immunization, before challenge and at the end of the experiment sera from each gosling were collected and examined for presence of antibodies against antigens of the vaccine strains.

Results

Vaccination of 5-week-old goslings with various lots of *mycoplasma* vaccine did not cause any adverse effect. Challenge of vaccinated gosling groups caused only mild lesions in comparison with non-vaccinated gosling groups. Both number of goslings with pathological lesions and lesion cores were in vaccinated groups significantly lower evaluated based on the score of pathological lesion versus the number of goslings with lesions (in the range of 19/6 8/8, 5/3 and 3/3) as compared to those in control challenged group (66/9). The protection effect of vaccines has been also demonstrated by significantly lower rates of isolation of *mycoplasmas* from inner organs of vaccinated goslings in contrast to those results obtained in non-vaccinated control groups.

Serological examination of gosling showed that background of OD values before vaccination varied between 0.186 and 0.224. Three weeks after immunization with OD values of antibodies reached (0.779-0.767) before the challenge, while that of the non-vaccinated group remained low (0.198-0.216).

Example 8

Combined Usage of *Mycoplasma* Vaccine with Parvovirus Vaccine Deparphylin

Parvovirus infection is highly spread in goose flocks and causes significant economic losses. Therefore, it is necessary to immunize geese every year against parvovirus infection. We examined if simultaneous immunization of geese against *mycoplasma* and parvovirus infections can be accomplished and to see if the co-administration of the two vaccines inhibits the serological response of birds induced by *mycoplasma* vaccine. For that purpose six groups of two years old geese (10 geese/group) which never have received *mycoplasma* vaccine were formed: Group 1 was immunized only with Deparphylin (Sanofi-Phylaxia, Budapest, Hungary) two times in a period of two weeks according to manufacture recommendation. Group 2 was vaccinated with *mycoplasma* vaccine twice in a part of two weeks subcutaneously. Group 3 was vaccinated with Deparphylin and *mycoplasma* vaccine. Deparphylin was administered first, then a week later *mycoplasma* vaccine was administered. In the third week again, Deparphylin was administered and in the fourth week *mycoplasma* vaccine was used for vaccination. Group 4 was vaccinated also with Deparphylin and *mycoplasma* vaccine. In the first week and in the third week both vaccines were administered at the same time on different side of the body. Group 5 was vaccinated with Deparphylin and *mycoplasma* vaccine. First week geese were inoculated with Deparphylin and with *mycoplasma* vaccines on different side of the body at the same time; administration of Deparphylin and the *mycoplasma* vaccines was repeated 3 weeks later.

Blood serum samples were collected and tested before vaccination, two weeks after first *mycoplasma* vaccination and two weeks after second *mycoplasma* vaccination. Antibodies to parvovirus were examined by neutralization test and antibodies to *mycoplasma* strain were tested by indirect ELISA.

Results

Data of this experiment show that if the geese are not immunized, background of OD values of antibodies against *mycoplasma* varied between 0.231 and 0.276. In case of testing antibodies against *mycoplasma*, if the birds were not immunized, the OD values remained low. In *mycoplasma* vaccinated animals the OD values increased significantly already after one month post vaccination in comparison with original OD and OD values of non-vaccinated group and remained high for another 6 months. When Deparphylin and *mycoplasma* vaccine was used on separate weeks the OD values became significantly higher (0.442-0.537) than in the case of using *mycoplasma* vaccine alone. Neither a positive effect nor a negative effect was noticed in case of using both vaccines at the same time.

Example 9

Evaluation of Safety and Efficacy of Vaccine in Ducks

Sixty 4 weeks old ducks were distributed into 6 groups. Body weights of the groups did not differ from each other. Group A was immunized with 2×0.5 ml of the vaccine (composed of killed and inactivated *M. anatis* combined with a mineral oil adjuvant), Group B was immunized with 1.0 ml of vaccine (composed of killed and inactivated *M. anatis* combined with a mineral oil adjuvant), Group C was immunized with 1.0 ml vaccine (composed of killed and inactivated type 1220 *mycoplasma* combined with a mineral oil adjuvant), Group D with 1.0 ml of vaccine (composed of killed and inactivated type 1220 *mycoplasma* and *M. anseris* combined with a mineral oil adjuvant). Group E and F remained without immunization. After 21 days all ducks were challenged with the combined vaccine strain *mycoplasma* aerosol matched for each group's vaccine strains (10 ml culture, $10^7$ cfu/ml). Afterward the birds were kept in cages and examined for clinical signs. At fourteen days post challenge the birds were necropsied and lesions (tracheitis, airsacculitis, peritonitis) were scored as accepted for *mycoplasma* infections of chickens. An attempt was made to isolate *mycoplasma* from inner organs. Body weight gain and serological response were also analyzed.

Results

After challenge ducks showed lacrimation and conjunctivitis. The group of non-immunized but challenged groups had significantly lesser body weight in comparison with those of immunized groups. No difference was noticed between average body weights and weight gains of the immunized groups independently whether they were immunized with the different vaccines. Score of pathological lesions were low (2-5) in comparison with those recorded in the non-vaccinated groups (18-28). The vaccinated animals showed positive serological response when compared to the non-immunized groups prior to challenge.

In histological sections of mucosal membranes infiltration by polymorphonuclear cells was less pronounced and less thickened in immunized groups than in non-immunized birds. Lymphofollicular foci were mostly expressed in control ducks. Isolation rates from organs of vaccinated groups were lower (3, 5, 4 or 0.1, 0.1.) than in the non-vaccinated groups (25, 19 or 8 and 9).

Example 10

Comparison of Efficacy of Vaccine A (Containing *Mycoplasma* sp. 1220 Strain) and Vaccine B (Combining *Mycoplasma* sp. 1220 Strain and *M. anseris*) on Body Weight, Macroscopic Lesions, and Histological Lesions in Geese, and Results of Isolation of *Mycoplasmas* from Organs of Geese after Challenge with *Mycoplasma* sp. 1220 Strain Four groups of one year old geese were selected for the experiment. Group 1 was immunized by vaccine A containing strain of *M.* sp. 1220 type, Group 2 was immunized with vaccine B containing a strain of *M.* sp. 1220 type plus a strain of *M. anseris*. Group 3 and 4 were injected with PBS. Three weeks post vaccination all groups were challenged with strain of 1220 type intra air sac. Two weeks later all groups were necropsied and examined for presence of macroscopic and histological lesions as well as for colonization of organs (air sac, lung liver, spleen) of geese with *mycoplasmas*. Before immunization and at the end of the study body weights were measured.

Results

After challenge in the group vaccinated with vaccine A body weights increased significantly, while in the group vaccinated with the group B no change in body weight was seen. In the control groups body weights decreased significantly post challenge.

The number of geese with lesions and lesions scores as well as isolation rate from air sacs, lung liver and spleen were very low in the groups in comparison with non-immunized group. Results of the group immunized with the vaccine B were lower than those in control group but a little higher than in those of the group vaccinated with vaccine A.

The results show the vaccination with combined vaccine gave less protection against the challenge than vaccine contained only strain 1220 type

TABLE 1

Comparison of Efficacy of Vaccine A Containing M. sp. 1220 Strain and Vaccine B Combining M. sp. 1220 Strain and *M. anseris* on Body Weight After Challenge with M. sp. 1220 Strain

| Vaccine | Body weight | Vaccinated challenged | Non-vaccinated challenged |
|---|---|---|---|
| A | Before challenge | 5.56 +/_0.59 | 5.52 +/− 0.61 |
| | At the end of study | 6.38 +/_0.69^*** | 4.02 +/− 0.45 |
| B | Before challenge | 5.52 +/− 0.81 | 5.50 +/− 0.73 |
| | At the end of study | 5.58 +/− 0.80^*** | 4.55 +/− 0.75 |

TABLE 2

Comparison of Efficacy of Vaccine A Containing *M.* sp. 1220 Strain and Vaccine B Combining *M.* sp. 1220 Strain and *M. anseris* on Macroscopic Lesions and Histological Lesions of Lung in Geese and Results of Isolation of Mycoplasmas from Organs of Geese Induced by Challenge with *M.* sp. 1220 Strain

| | | Vaccinated with the vaccine A | | Vaccinated with the vaccine B | | Non-vaccinated challenged | |
|---|---|---|---|---|---|---|---|
| | Parameters | No. of geese with positive results | Lesion scores | No. of geese with positive results | Lesion scores | No. of geese with positive results | Lesion scores |
| Macroscopic lesions | Left air sac | $3^{\#***}$ | 3^* | 5 | 15 | 10 | 36 |
| | Right air sac | $1^{\#***}$ | 1^* | 4 | 12 | 9 | 27 |
| | Peritoneum | $2^{\#***}$ | 2^* | 4 | 14 | 8 | 26 |
| Histological lesions of lung | Interstitial pneumonia | $5^{\#***}$ | 5^*** | 5 | 10 | 9 | 28 |
| | Lymphoid follicles | $0^{\#***}$ | 0^*** | 3 | 6 | 9 | 19 |
| | Serous pneumonia | $0^{\#***}$ | 0^*** | 5 | 10 | 9 | 16 |
| Reisolation of mycoplasma from | Left air sac | $1^{\#***}$ | ^*** | 4 | — | 10 | — |
| | Lung | $0^{\#***}$ | ^*** | 4 | — | 9 | — |
| | Liver | $0^{\#***}$ | ^*** | 4 | — | 8 | — |
| | Spleen | $1^{\#***}$ | ^**^^ | 1 | — | 6 | — |

REFERENCES

The following references are cited by parenthetical number above. These references are incorporated herein in their entirety by this reference. In addition, all publications, patents, and published patent applications mentioned in this specification are indicative of the level of skill of those skilled in the art to which this invention pertains. All publications and patents are herein incorporated by reference to the same extent if each individual publication or patent application were specifically and individually indicated to be incorporated by reference.

1. Bednarczyk, M., and Rosinski, A. Comparison of Egg Hatchability and In Vitro Survival of Goose Embryos of Various Origins Poultry Science 78:579-585. 1999.
2. Beemer, A. M., E. S. Kuttin, and Z. Katz. Epidemic Venereal Disease Due to Candida albicans in Geese in Israel. Avian Diseases. Vol. 17: 639-649. 1973.
3. Behr, K. P, and K. H. Hinz. Penile inflammation in ganders. Dtsch. Tierarztl. Wochenschr. 96:140-143. 1989
4. Bencina, D., D. Dorrer, and T. Tadina. *Mycoplasma* species isolated from six avian species. Avian Pathol. 16: 653-664.1987.
5. Bencina, D., T. Tadina, and D. Dorrer. Natural infection of geese with *Mycoplasma gallisepticum* and *Mycoplasma synoviae* and egg transmission of the *mycoplasmas*. Avian Pathol. 17: 925-928. 1988.

6. Bradbury, J. M., A. Vuillaume, J. Dupiellet, M. Forrest, J. Bind, and G. Gaillard-Perrin. Isolation of *Mycoplasma cloacale* from a number of different avian hosts in Great Britain and France. Avian Pathol. 16: 183-186. 1987.
7. Bradbury, J. M., F. T. W. Jordan, T. Shimizu, L. Stipkovits, and Z. Varga. *Mycoplasma anseris* strain novum. found in geese. Int. J. Syst. Bact. 38:74-76. 1988.
8. Bradbury, J. M., O. M. S. Abdul-Wahab, C. A. Yavary, J-P. Dupiellet, and J. M. Bové. *Mycoplasma imitans* sp. nov. is related to *Mycoplasma gallisepticum* and found in birds. Int. J. Syst. Bact. 43: 721-728. 1993.
9. Buntz, B., J. M. Bradbury, A. Vuillaume, and D. Rousselot-Paillet. 1986. Isolation of *Mycoplasma gallisepticum* from geese. Avian Pathol. 155:615-617. 1986.
10. Buntz, B. Isolement et mise en evidence du pouvoir pathogene de M. gallisepticum chez l'oie (Anser anser). PhD Thesis, Villenave d'Oron, France, Universite du Bordeaux II. 1987.
11. Dobos-Kovacs, M., G. Czifra, Z. Varga, and L. Stipkoivts. A lúd phallusgyulladása. I. Újabb adatok a betegség morphogeneziséhez. Magy.Ao. Lapja, 40:49-57. 1985.
12. Dobos-Kovacs, M., Z. Varga, G. Czifra, and L. Stipkovits. Salpingitis in geese associated with *Mycoplasma* sp. strain 1220. Avian Pathol. 38:1-5. 2009.
13. Dupiellet, J. P. Mycoplasmes et acholeplasmes des palmipedes a foie gras: isolement, caracterisation, etude du role dans la pathologie. Rapport D. E. A. de Pathologie. Villenave d'Oron, France, Universite de Bordeaux II. 1984.
14. Dupiellet, J. P. Mycoplasmes de l'oie et du canard: constrution a l'etude serologique et moleculaire de souches aparentees a *Mycoplasma gallisepticum*. PhD Thesis, Villenave d'Oron, France, Universite de Bordeaux II. 1988.
15. Dupiellet, J. P., A. Vuillaume, D. Rousselot, J. M. Bove, and J. M. Bradbury. Serological and molecular studies on *Mycoplasma gallisepticum* strains. Zbl. Bakteriol. Mikrobiol. Hyg. Suppl 20: 859-864. 1990.
16. Evans, T. Global Poultry Trends-Asia dominates world duck and goose meat production. The Poultry Site Newsletter. 8. 2011.
19. Gaillard-Perrin G., P. Nougayrede, and A. Vuillaume. Caracterisation de quelques souches de mycoplasmes isolees chez l'oie et le canard dans de Landes. Revue de Med. Vet. 134: 97-102. 1983.
20. Hinz, K. H., H. Pfutzner, and K. P. Behr. Isolation of *mycoplasmas* from clinically healthy adult breeding geese in Germany. Zbl. Veterinärmedizin. B. 41: 145-147. 1994.
21. Janiszewska, M. Changes in body weight and tissue components of white Italian geese during the rearing period. Acta Acad. Agricult. Techn. Olst., Zoot., 37 Suppl., A:1-39. (in Polish). 1993.
22. Jannan, J., L. Bodi, G. Agota, L. Bardos, P. Rudas, J. Kozak, and M. Karsai. Relationship between force feeding and some physiological parameters in geese bred for fatty liver. Acta Vet. Hung. 48:89-92. 2004.
23. Kempf, I. The Mycoplasmsma of ducks. Recueil de Medecine Veterinaire. 166: 1111-1115. 1990.
24. Kisary, J., A. A. El-Ebeedy, and L. Stipkovits. II. Studies on pathogenicity of *Mycoplasmas* in goslings and goose and chicken embryos. Avian Pathol. 5:15-20. 1976.
25. Kleven, S. H., and D. P. Anderson. In vitro activity of various antibiotics against *Mycoplasma synoviae*. Avian Dis. 15:551-557. 1971.
26. Kleven, S. H., D. D. King, and P. David, and P. Anderson. Airsacculitis in Broilers from *Mycoplasma synoviae*: Effect on Air-Sac Lesions of Vaccinating with Infectious Bronchitis and Newcastle Virus. Avian Disease. Vol. 16: 915-924. 1972.
27. Kosovac, A., and S. Djurisic. 1970. Disease of female genital tract of geese and mycoplasmosis. IVth Cong. of WVPA 429-44. 1970.
28. Lin, M., S. Liu, W. Su, Y. Lan, I. Chung, M. Y. Lin, S. S. Liu, S. W. S. Su, Y. C. Lan, and I. C. Chung. Isolation of avian *mycoplasmas* from geese in Taiwan. J. the Chinese Soc. of Vet. Sci. 21: 347-353. 1995.
29. Marjánková, K., K. Křivanec, and J. Zajiček. Mass occurrence of necrotic inflammation of the penis in ganders caused by phycomycetes. Mycopathologia. 66, Numbers 1-2, 21-26, DOI: 10.1007/BF00429588
30. Pingel H. Duck and geese production around the world. World Poultry. 20:26-28. 2004.
31. Report of the Scientific Committee on animal health and welfare aspects of the production of foie gras in ducks and geese. EU. 1998.
32. Spiller, S. V. The effect of egg weight, parents age, body weight and reproduction traits of offspring's liver and meat production in geese. Ph.D., thesis. Szent Istvan University, Hungary. 2005.
33. Stipkovits, L., A. A. El-Ebeedy, J. Kisary, and L. Varga. *Mycoplasma* infection of geese. I. Incidence of *mycoplasmas* and *acholeplasmas* in geese. Avian Pathol. 4:35-43. 1075.
34. Stipkovits, L., J. M. Bove, M. Rousselot, P. Larrue, M. Labat, and A. Vuillaume. Studies on *Mycoplasma* infection of laying geese. Avian Pathol. 14:57-68. 1984a.
35. Stipkovits, L., Z. Varga, M. Dobos-Kovács, and M. Santa. Biochemical and serological examination of some *Mycoplasma* strains of goose origin. Acta Vet. Hung. 32:117-125. 1984b.
36. Stipkovits, L., and I. Kempf I. Mycoplasmoses in poultry. Rev. Sci. Tech. 15: 1495-1525. 1996.
37. Stipkovits, L., Z. Varga, G. Czifra, and M. Dobos-Kovacs. Occurence of mycoplamas in geese affected with inflammation of the cloaca and phallus. Avian Pathol. 15: 289-299. 1986.
38. Stipkovits, L., Z. Varga, R. Glavits, F. Ratz, and E. Molnar. Pathological and immunological studies on goose embryos and one-day-old goslings experimentally infected with a *mycoplasma* strain of goose origin. Avian Pathol. 16: 453-468. 1087.
39. Szep, I. I., M. M. Pataky, and J. J. Bögre. Recent practical and experimental observations on the infectious inflammatory disease of cloaca and penis in geese. Acta Vet Acad Sci Hung 27:195-202. 1979
40. Varga, Z., L. Stipkovits, M. Dobos-Kovacs. and G. Czifra. Biochemical and serological study of two *mycoplasma* strains isolated from geese. Arch Exp Veterinärmed. 43: 33-736. 1989.
41. Varga, Z, L. Stipkovits, M. Dobos-Kovács, and G. Czifra. Biochemical and serological characteristics of goose *Mycoplasmas*. Zbl. Bact., Suppl. 20:867-868. 1990.
42. Varga, Z., M. Dobos-Kovács, G. Czifra, and L. Stipkovits. Generating of salpingitis and peritonitis in geese by *mycoplasma* sp. strain 1220. Avian Pathol. 38:239-243. 2009.
43. Volokhov, D. V., Z. Varga, M. May, N. Ferguson-Noel, D. R. Brown, V. E. Chizhikov, J. M. Bradbury, S. Szathmary, and L. Stipkovits. *Mycoplasma anserisalpingitis* sp. nov., from domestic geese (Anser anser domesticus) with *mycoplasma*-associated reproductive pathology. IOM Congress. 2010.

ADVANTAGES OF THE INVENTION

The present invention provides vaccine formulations that are effective in controlling mycoplasmal infections in waterfowl, especially geese and ducks. Vaccine formulations according to the present invention reduce mortality among flocks of geese and ducks, increase body weight of vaccinated birds, and increase breeding efficacy and egg-laying in vaccinated birds. Vaccine formulations according to the present invention can be used together with other vaccines in use for vaccination of waterfowl, such as the vaccine for parvovirus. Vaccine formulations according to the present invention are well tolerated and do not produce significant side effects.

Vaccine formulations according to the present invention possess industrial applicability as pharmaceutical compositions for avian use. Methods of vaccinating waterfowl according to the present invention employing vaccine formulations according to the present invention possess industrial applicability as methods of treating non-human animals.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, and literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

What is claimed is:

1. A vaccine that is protective against mycoplasmal disease of a waterfowl comprising at least one inactivated waterfowl mycoplasmal strain wherein no virus capable of reproduction or proliferation is included in the vaccine, the vaccine comprising at least one pharmaceutically acceptable adjuvant selected from the group consisting of: an aluminum hydroxide-oil emulsion; a vegetable oil-water emulsion; a fish oil-water emulsion; *Escherichia coli* J5, dextran sulfate; a synthetic polymer; polyacrylic acid; saponin; a long-chain polydisperse β(1,4)-linked mannan polymer interspersed with O-acetylated groups; a deproteinized cell wall extract from a non-pathogenic strain of *Mycobacterium*; muramyl dipeptide β-propiolactone; and aluminum phosphate, wherein the at least one inactivated waterfowl mycoplasmal strain is selected from the group consisting of: *Mycoplasma* sp. strain 1220; *Mycoplasma anseris; Mycoplasma anatis; Mycoplasma cloacale; Mycoplasma imitans; Acholeplasma modicum*; and *Acholeplasma axantum* and wherein the waterfowl is selected from the group consisting of a duck and a goose.

2. The vaccine of claim 1 wherein the vaccine further comprises at least one pharmaceutically acceptable excipient.

3. The vaccine of claim 1 wherein the vaccine is protective against mycoplasmal infection for a duck.

4. The vaccine of claim 1 wherein the vaccine is protective against mycoplasmal infection for a goose.

5. A vaccine that is protective against mycoplasmal disease of a waterfowl comprising two or more strains of inactivated waterfowl *mycoplasma*, such that the mycoplasmal strain in the vaccine is inactivated and no virus capable of reproduction or proliferation is included in the vaccine, the vaccine comprising at least one pharmaceutically acceptable adjuvant selected from the group consisting of: an aluminum hydroxide-oil emulsion; a vegetable oil-water emulsion; a fish oil-water emulsion; *Escherichia coli* J5, dextran sulfate; a synthetic polymer; polyacrylic acid; saponin; a long-chain polydisperse β(1,4)-linked mannan polymer interspersed with O-acetylated groups; a deproteinized cell wall extract from a non-pathogenic strain of *Mycobacterium*; muramyl dipeptide β-propiolactone; and aluminum phosphate.

6. The vaccine of claim 5 wherein one of the strains of inactivated waterfowl *mycoplasma* is selected from the group consisting of: *Mycoplasma* sp. strain 1220; *M. anseris; M. anatis; M. cloacale; M. imitans*; and *M. synoviae*.

7. A vaccine that is protective against mycoplasmal disease of a waterfowl comprising at least one inactivated waterfowl mycoplasmal strain wherein no virus capable of reproduction or proliferation is included in the vaccine, the vaccine comprising at least one pharmaceutically acceptable adjuvant selected from the group consisting of: an aluminum hydroxide-oil emulsion; a vegetable oil-water emulsion; a fish oil-water emulsion; *Escherichia coli* J5, dextran sulfate; a synthetic polymer; polyacrylic acid; a polyamino acid; a copolymer of two or more amino acids; saponin; an emulsion of mycobacterial cell wall fractions comprising trehalose dimycolate and muramyl dipeptide; N,N-dioctadecyl-N',N'-bis(2-hydroxyethyl)propanediamine; a long-chain polydisperse β(1,4)-linked mannan polymer interspersed with O-acetylated groups; a deproteinized cell wall extract from a non-pathogenic strain of *Mycobacterium*; and aluminum phosphate, wherein the inactivated mycoplasmal strain is selected from the group consisting of *Mycoplasma anseris* and *Mycoplasma* sp. strain 1220.

* * * * *